US012758164B2

(12) United States Patent
Kakimoto et al.

(10) Patent No.: US 12,758,164 B2
(45) Date of Patent: Oct. 13, 2026

(54) BED APPARATUS AND MEDICAL DIAGNOSTIC SYSTEM

(71) Applicant: FUJIFILM Corporation, Tokyo (JP)

(72) Inventors: Masanori Kakimoto, Tokyo (JP); Satoshi Iizuka, Tokyo (JP); Mikio Mochitate, Tokyo (JP); Takayuki Kanamori, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 17 days.

(21) Appl. No.: 18/930,977

(22) Filed: Oct. 29, 2024

(65) Prior Publication Data

US 2025/0143655 A1 May 8, 2025

(30) Foreign Application Priority Data

Nov. 2, 2023 (JP) ................................ 2023-188415

(51) Int. Cl.
*A61B 6/04* (2006.01)

(52) U.S. Cl.
CPC .................................. *A61B 6/0407* (2013.01)

(58) Field of Classification Search
CPC ...... A61B 6/0407; A61B 6/032; A61B 6/0487
See application file for complete search history.

(56) References Cited

U.S. PATENT DOCUMENTS 3,623,617 A * 11/1971 Nemessanyi ........... B66F 7/065 414/640
4,181,858 A * 1/1980 Moore ................. A61B 6/4035 378/18
4,567,894 A * 2/1986 Bergman ............... A61B 5/055 505/879
4,858,888 A * 8/1989 Cruz ....................... B66F 7/065 254/122
4,914,682 A * 4/1990 Blumenthal ......... A61B 6/0487 378/208
5,111,546 A * 5/1992 Hahn ................. B65G 69/2823 14/71.3
5,460,460 A * 10/1995 Alexander ................ B66F 7/08 14/71.3
6,761,248 B1 * 7/2004 Harbison .............. B66F 11/042 182/69.5

(Continued)

FOREIGN PATENT DOCUMENTS

| | | |
|---|---|---|
| CN | 104173050 | 12/2014 |
| CN | 115251892 | 11/2022 |

(Continued)

OTHER PUBLICATIONS

"First Office Action of China Counterpart Application", issued on Feb. 28, 2026, with English translation thereof, p. 1-p. 17.

*Primary Examiner* — Aaron R Eastman
(74) *Attorney, Agent, or Firm* — JCIPRNET

(57) ABSTRACT

There are provided a bed apparatus and a medical diagnostic system capable of reducing a capacity of an actuator while lowering a lowest height of a tabletop surface. A jack arm that connects a first arm and a rod of a pantograph arm in an up-down direction is provided, an upper end part of the jack arm is connected to an upper end part of the rod, and a lower end part of the jack arm is rotationally movably connected to a position between an intersection part and an upper end part of the first arm.

6 Claims, 7 Drawing Sheets

(56) References Cited

U.S. PATENT DOCUMENTS

| | | | | |
|---|---|---|---|---|
| 7,543,989 | B2 * | 6/2009 | Hoth | A61G 13/06<br>378/177 |
| 8,015,638 | B2 * | 9/2011 | Shimada | A47C 19/045<br>108/147 |
| 8,469,152 | B2 * | 6/2013 | Olsen | B66F 7/065<br>414/800 |
| 9,777,755 | B2 * | 10/2017 | Lowe | F15B 15/26 |
| 10,499,730 | B2 * | 12/2019 | Kim | A47B 21/02 |
| 2008/0047068 | A1 * | 2/2008 | Zakrzewski | A61B 6/0487<br>5/611 |
| 2013/0341984 | A1 * | 12/2013 | Olesen | A61G 5/1059<br>254/122 |
| 2021/0229537 | A1 * | 7/2021 | Piche | B60P 7/02 |

FOREIGN PATENT DOCUMENTS

| | | |
|---|---|---|
| GB | 2434526 | 12/2007 |
| JP | 2002159539 | 6/2002 |
| JP | 2009297145 | 12/2009 |
| JP | 2019115980 | 7/2019 |

* cited by examiner

BED APPARATUS AND MEDICAL DIAGNOSTIC SYSTEM

CROSS-REFERENCE TO RELATED APPLICATION

The present application claims priority under 35 U.S.C § 119(a) to Japanese Patent Application No. 2023-188415 filed on Nov. 2, 2023, which is hereby expressly incorporated by reference, in its entirety, into the present application.

BACKGROUND OF THE INVENTION

1. Field of the Invention

The present invention relates to a bed apparatus and a medical diagnostic system, and particularly relates to a bed apparatus and a medical diagnostic system used for a medical image capturing apparatus.

2. Description of the Related Art

In a case in which a medical image of a subject is captured by the medical image capturing apparatus, the capturing is performed by using a dedicated bed apparatus installed in an examination room. As the medical image capturing apparatus, a magnetic resonance imaging (MRI) apparatus, an X-ray computed tomography (CT) apparatus, and the like are known.

JP2009-297145A discloses a bed apparatus that moves a tabletop up and down by driving an X-shaped link mechanism by extending and retracting a jack.

JP2019-115980A discloses a bed apparatus that moves a middle floor (tabletop) up and down by extending and retracting a telescopic cover by extending and retracting a piston rod of a hydraulic cylinder.

In the field of the bed apparatus, it is desirable to lower a lowest height of a tabletop surface in order to reduce a burden on the subject. The tabletop surface is an upper surface of the tabletop on which the subject is placed.

SUMMARY OF THE INVENTION

The bed apparatus of JP2009-297145A has a configuration in which a thrust force is applied in a direction inclined with respect to an up-down direction to raise and lower the tabletop, so that it is possible to lower the lowest height of the tabletop surface. However, there is a problem in that an actuator having a large capacity (power) is required because a thrust force required near the lowest height of the tabletop surface becomes large.

Meanwhile, the bed apparatus of JP2019-115980A has a configuration in which the tabletop is raised and lowered (ascend and descend) by applying a constant thrust force in the up-down direction, so that it is possible to reduce the capacity of the actuator. However, there is a problem in that the lowest height of the tabletop surface becomes high because a size of the actuator is limited.

The present invention has been made in view of such circumstances, and an object of the present invention is to provide a bed apparatus and a medical diagnostic system capable of reducing a capacity of an actuator while lowering a lowest height of a tabletop surface.

According to a first aspect of the present invention, there is provided a bed apparatus comprising: a base member; an ascending and descending member; an X-shaped pantograph arm including a first arm member and a second arm member that is connected to the first arm member at an intersection part so as to be rotationally movable with respect to the first arm member, the X-shaped pantograph arm connecting the ascending and descending member to the base member such that the ascending and descending member is able to ascend and descend in an up-down direction; and an actuator that drives the pantograph arm, in which the actuator includes a driving source, a rod member that moves in the up-down direction by power of the driving source, and a first connecting member that connects the rod member and the first arm member in the up-down direction and that has an upper end part connected to an upper end part of the rod member and a lower end part rotationally movably connected to a position between the intersection part and an upper end part of the first arm member.

With the bed apparatus according to the first aspect, the configuration is adopted in which the first connecting member that connects the first arm member of the pantograph arm and the rod member in the up-down direction is provided, and the upper end part of the first connecting member is connected to the upper end part of the rod member and the lower end part of the first connecting member is rotationally movably connected to the position between the intersection part and the upper end part of the first arm member, so that it is possible to reduce the capacity of the actuator while lowering the lowest height of the tabletop surface.

It is preferable that a second aspect of the present invention provides the bed apparatus according to the first aspect, which further comprises: a second connecting member that connects the actuator and the second arm member in the up-down direction and that has an upper end part rotationally movably connected to a position between the intersection part and a lower end part of the second arm member and a lower end part connected to a lower end part of the actuator.

It is preferable that a third aspect of the present invention provides the bed apparatus according to the first aspect, which further comprises: a horizontal movement support portion that supports the actuator to be movable in a horizontal direction.

It is preferable that a fourth aspect of the present invention provides the bed apparatus according to any one of the first to third aspects, in which the ascending and descending member has an escape hole for allowing the upper end part of the rod member to escape upward from the ascending and descending member in a case in which the ascending and descending member is moved downward.

According to a fifth aspect of the present invention, there is provided a medical diagnostic system comprising: the bed apparatus according to any one of the first to third aspects; and a medical image capturing apparatus.

It is preferable that a sixth aspect of the present invention provides the medical diagnostic system according to the fifth aspect, in which the ascending and descending member of the bed apparatus has an escape hole for allowing the upper end part of the rod member to escape upward from the ascending and descending member in a case in which the ascending and descending member is moved downward.

According to the present invention, it is possible to reduce a capacity of an actuator while lowering a lowest height of a tabletop surface.

DESCRIPTION OF THE PREFERRED EMBODIMENTS

Hereinafter, embodiments of a bed apparatus and a medical diagnostic system according to the present invention will be described with reference to the accompanying drawings.

For convenience of description of configurations of the bed apparatus and the medical diagnostic system according to the embodiment, a scale of each element shown in the accompanying drawings may be different from an actual scale of the element. Therefore, the illustrated elements are not limited to a specific scale illustrated on the drawings.

Figure 1:
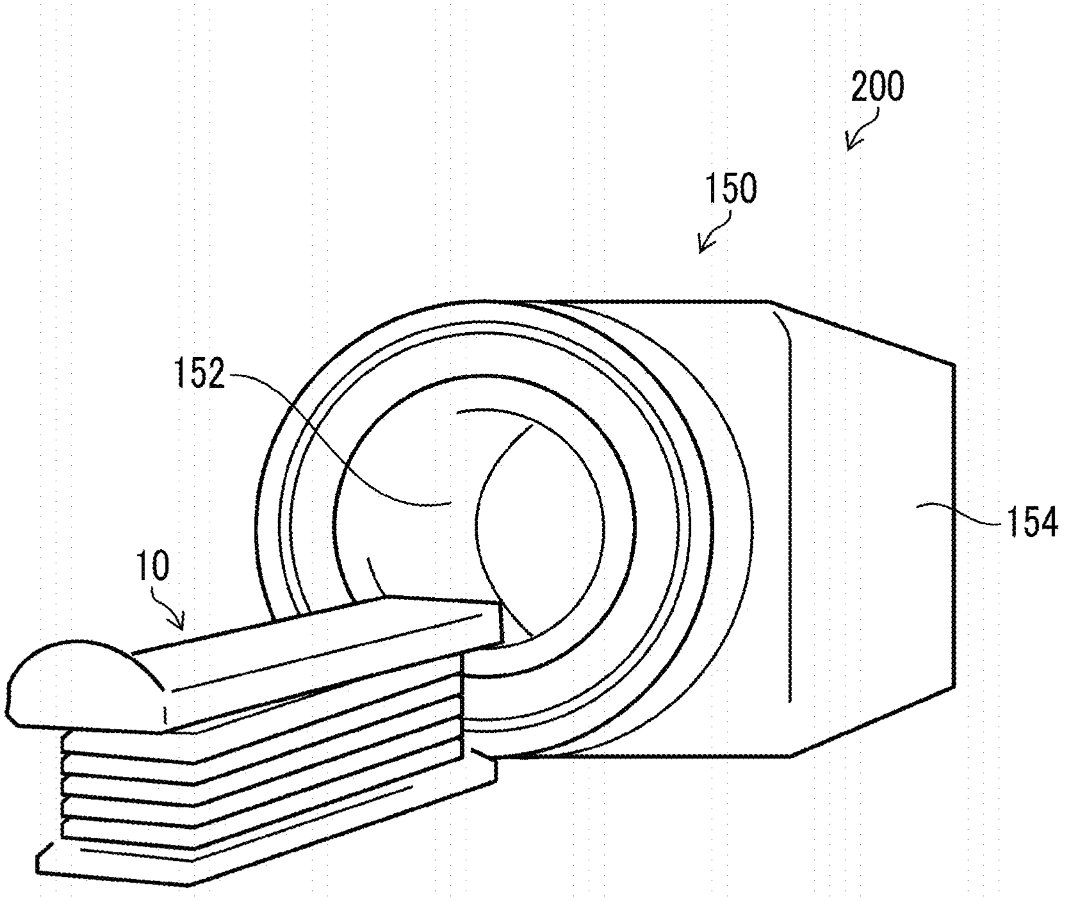
FIG. 1 is a configuration diagram of a medical diagnostic system according to an embodiment.

FIG. 1 is an overall view of a medical diagnostic system 200 according to the embodiment. The medical diagnostic system 200 of the present example comprises a bed apparatus 10 according to the embodiment and an MRI apparatus 150. The MRI apparatus 150 comprises a gantry 154 having a bore 152 which is a cylindrical imaging space.

In the present example, the MRI apparatus 150 is used as an example of the medical image capturing apparatus, but the present invention is not limited to the MRI apparatus 150, and an X-ray CT apparatus, a positron emission tomography (PET) apparatus, a radiation therapy apparatus, or a particle beam therapy apparatus may be used. Hereinafter, the bed apparatus 10 according to the embodiment will be described.

Figure 2:
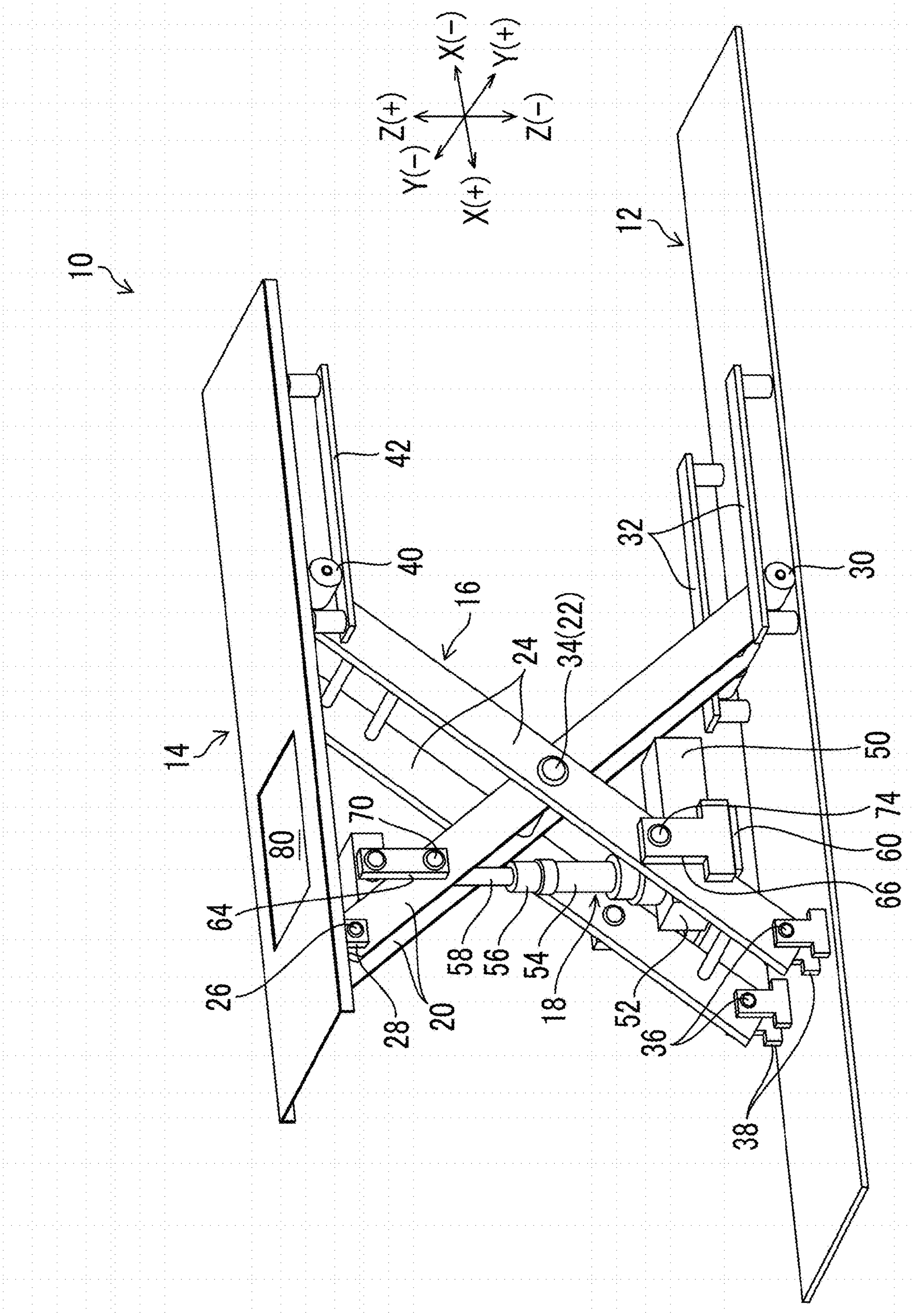
FIG. 2 is a perspective view showing main components of a bed apparatus according to the embodiment.

As shown in FIG. 2, the bed apparatus 10 according to the embodiment comprises a base 12 that is installed on a floor surface of an examination room, an upper frame 14, an X-shaped pantograph arm 16 that moves the upper frame 14 up and down with respect to the base 12, and a screw-type jack 18 that drives the pantograph arm 16. FIG. 2 shows a state in which the upper frame 14 is located at (raised to) the highest position.

Hereinafter, a configuration of the bed apparatus 10 according to the embodiment will be described in detail, but the description in the present specification will be made with reference to a three-dimensional orthogonal coordinate system of X, Y, and Z axes. In this case, an X axis direction indicates a horizontal direction, a Y axis direction indicates a horizontal direction orthogonal to the X axis direction, and a Z axis direction indicates an up-down direction orthogonal to the X axis direction and the Y axis direction. In addition, in FIG. 2, a left side of the bed apparatus 10 will be referred to as an X(+) direction, a right side will be referred to as an X(−) direction, a front side will be referred to as a Y(+) direction, a depth side will be referred to as a Y(−) direction, an upper side will be referred to as a Z(+) direction, and a lower side will be referred to as a Z(−) direction.

As described above, the bed apparatus 10 according to the embodiment comprises the base 12, the upper frame 14, the pantograph arm 16, and the screw-type jack 18.

The base 12 and the upper frame 14 are disposed to face each other in the Z axis direction, and are each configured as a plate-shaped member having a longitudinal axis in the X axis direction. The base 12 is an example of a base member according to the present invention, and the upper frame 14 is an example of an ascending and descending member according to the present invention. In addition, in FIG. 2, other members such as a tabletop attached to the upper frame 14 and a cover that covers the pantograph arm 16 and the screw-type jack 18 are not shown.

The pantograph arm 16 includes a pair of first arms 20 and a pair of second arms 24 that are connected to the pair of first arms 20 so as to be rotationally movable with respect to the pair of first arms 20 at an intersection part 22. The pantograph arm 16 is a member that connects the upper frame 14 to the base 12 such that the upper frame 14 is movable in the up-down (Z axis) direction. The pantograph arm 16 is an example of a pantograph arm according to the present invention.

The first arm 20 and the second arm 24 are each configured as an elongated plate-shaped member having a longitudinal axis. The first arm 20 and the second arm 24 are configured to have the same length in a longitudinal axis direction. The intersection part 22 is set at an intermediate position in the longitudinal axis direction of the first arm 20 and the second arm 24.

The pair of first arms 20 are disposed at positions overlapping each other in the Y axis direction, and the pair of second arms 24 are similarly disposed at positions overlapping each other in the Y axis direction. The pair of first arms 20 and the pair of second arms 24 are disposed to intersect each other between the base 12 and the upper frame 14 in an X-Z plane.

A shaft 26 extending along the Y axis is connected to an upper end part of the pair of first arms 20 on the upper frame 14 side. The shaft 26 is rotatably connected to a bearing unit 28 fixed to the upper frame 14. In the following description, the expression of "pair of" will be omitted. The same applies to the other pair of members such as the second arms 24.

A roller 30 that rotates about the Y axis is provided at a lower end part of the first arm 20 on the base 12 side. The roller 30 is connected to a rail 32 fixed to the base 12 in the X axis direction so as to be rotatable and slidably movable in the X direction.

The first arm 20 configured as described above can be moved rotationally in the X-Z plane with the shaft 26 as a rotational movement fulcrum. The first arm 20 is an example of a first arm member according to the present invention.

The second arm 24 is rotationally movably connected to the first arm 20 via a shaft 34 extending along the Y axis at the intersection part 22 intersecting the first arm 20. That is, the first arm 20 and the second arm 24 are connected so as to be rotationally movable with respect to each other in the X-Z plane via the shaft 34.

A shaft 36 extending along the Y axis is connected to a lower end part of the second arm 24 on the base 12 side. The shaft 36 is rotatably connected to a bearing unit 38 fixed to the base 12.

A roller 40 that rotates about the Y axis is provided at an upper end part of the second arm 24 on the upper frame 14 side. The roller 40 is connected to a rail 42 fixed to the upper frame 14 in the X direction so as to be rotatable and slidably movable in the X direction.

The second arm 24 configured as described above can be moved rotationally in the X-Z plane with the shaft 36 as a rotational movement fulcrum. The second arm 24 is an example of a second arm member according to the present invention.

Here, a positional relationship between the members constituting the bed apparatus 10 will be described.

Figure 3:
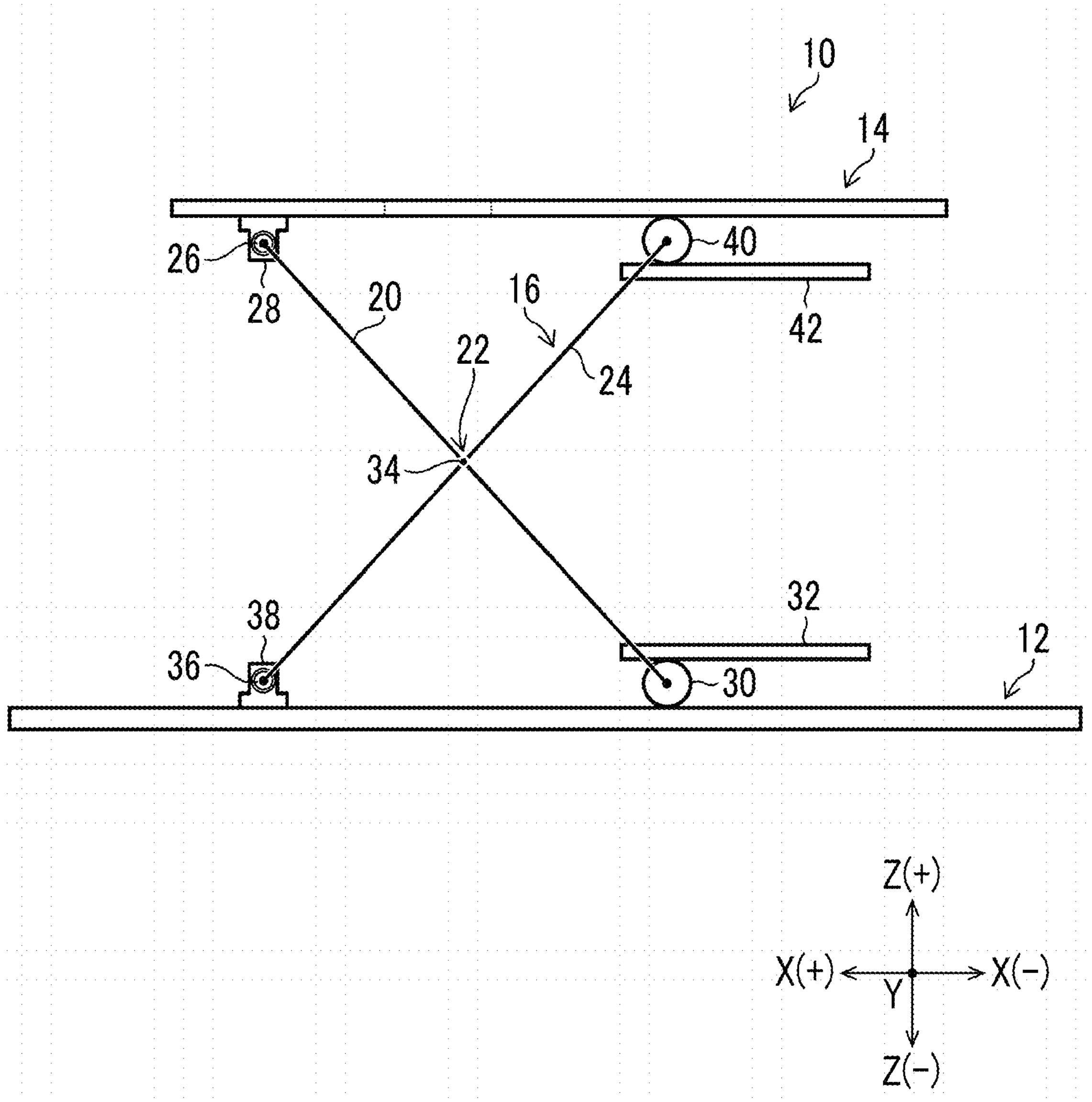
FIG. 3 is a schematic diagram showing a case in which an upper frame is located at the highest position.

FIG. 3 is a schematic diagram of the bed apparatus 10 showing a state in which the upper frame 14 is located at (raised to) the highest height (the same state as in FIG. 2). In other words, FIG. 3 is a schematic diagram of the bed apparatus 10 in a case in which a tabletop surface (not shown) is located at the highest height. In FIG. 3, the screw-type jack 18 (see FIG. 2) is not shown.

Figure 4:
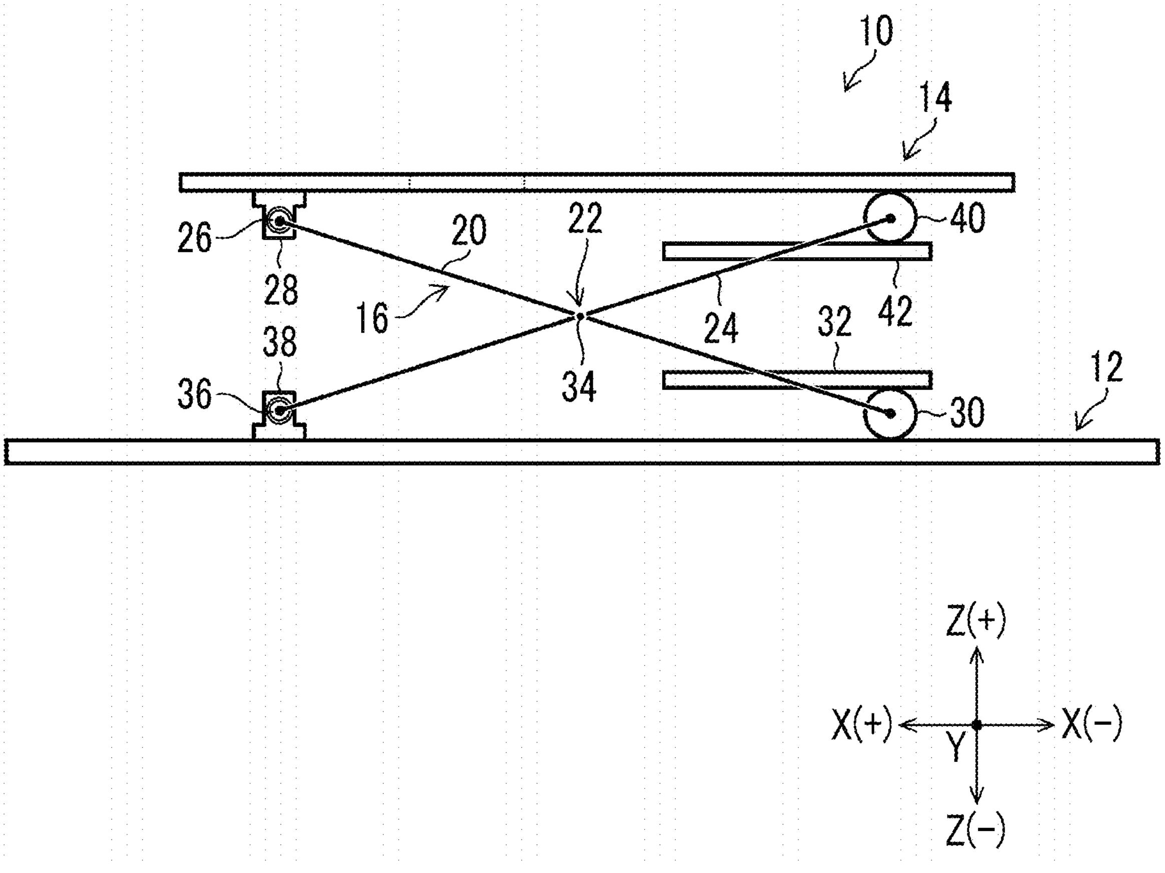
FIG. 4 is a schematic diagram showing a case where the upper frame is located at the lowest position.

In addition, FIG. 4 is a schematic diagram of the bed apparatus 10 showing a state in which the upper frame 14 is located at (lowered to) the lowest height. In other words, FIG. 4 is a schematic diagram of the bed apparatus 10 in a case in which a tabletop surface (not shown) is located at the lowest height. In FIG. 4, the screw-type jack 18 (see FIG. 2) is not shown.

As shown in FIGS. 3 and 4, the first arm 20 and the second arm 24 are connected so as to be rotationally movable with respect to each other via the shaft 34 at the intersection part 22. As described above, the intersection part 22 is set at an intermediate position in the longitudinal axis direction of each of the first arm 20 and the second arm 24. As a result, the shaft 26 and the shaft 36 are disposed on the same axis in the Z direction. In addition, the roller 40 and the roller 30 are disposed at positions spaced apart by an equal distance in the X axis direction from the shaft 26 and the shaft 36, and are disposed on the same axis in the Z direction.

In a case in which the pantograph arm 16 of FIG. 3 is lowered by a driving force of the screw-type jack 18 of FIG. 2, the rollers 40 and 30 move in the X(−) direction away from the shafts 26 and 36, and in conjunction with this movement, the upper frame 14 moves downward in the Z(−) direction approaching the base 12. As a result, the height of the upper frame 14 gradually decreases from the highest position shown in FIG. 3 to the lowest position shown in FIG. 4.

In addition, in a case in which the pantograph arm 16 of FIG. 4 is raised by a driving force of the screw-type jack 18 of FIG. 2, the rollers 40 and 30 move in the X(+) direction approaching the shafts 26 and 36, and in conjunction with this movement, the upper frame 14 moves upward in the Z(+) direction away from the base 12. As a result, the height of the upper frame 14 gradually increases from the lowest position shown in FIG. 4 to the highest position shown in FIG. 3.

Next, the screw-type jack 18 (see FIG. 2) that drives the pantograph arm 16 will be described.

Figure 5:
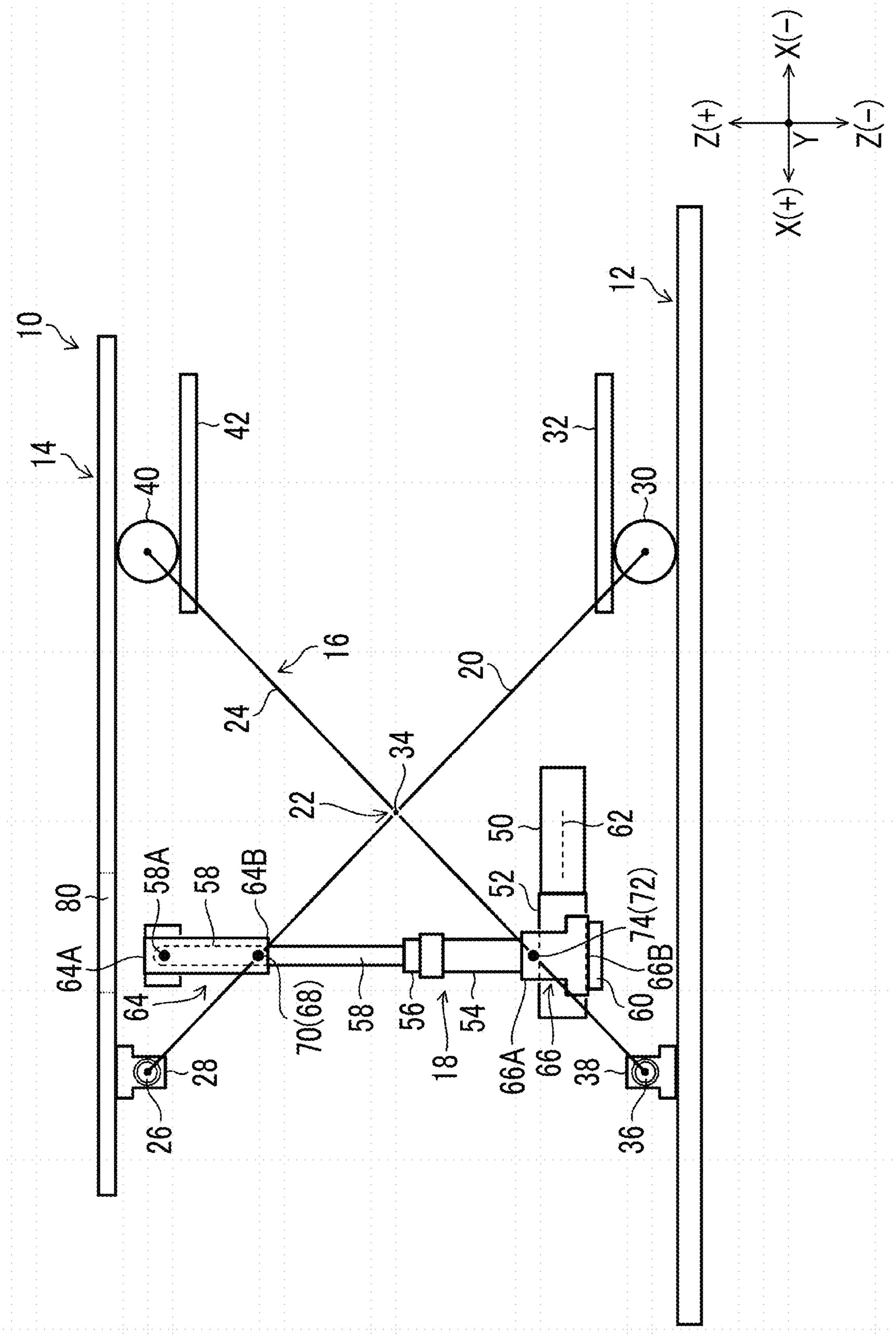
FIG. 5 is a schematic diagram showing a case in which the upper frame is located at the highest height by a screw-type jack.
Figure 6:
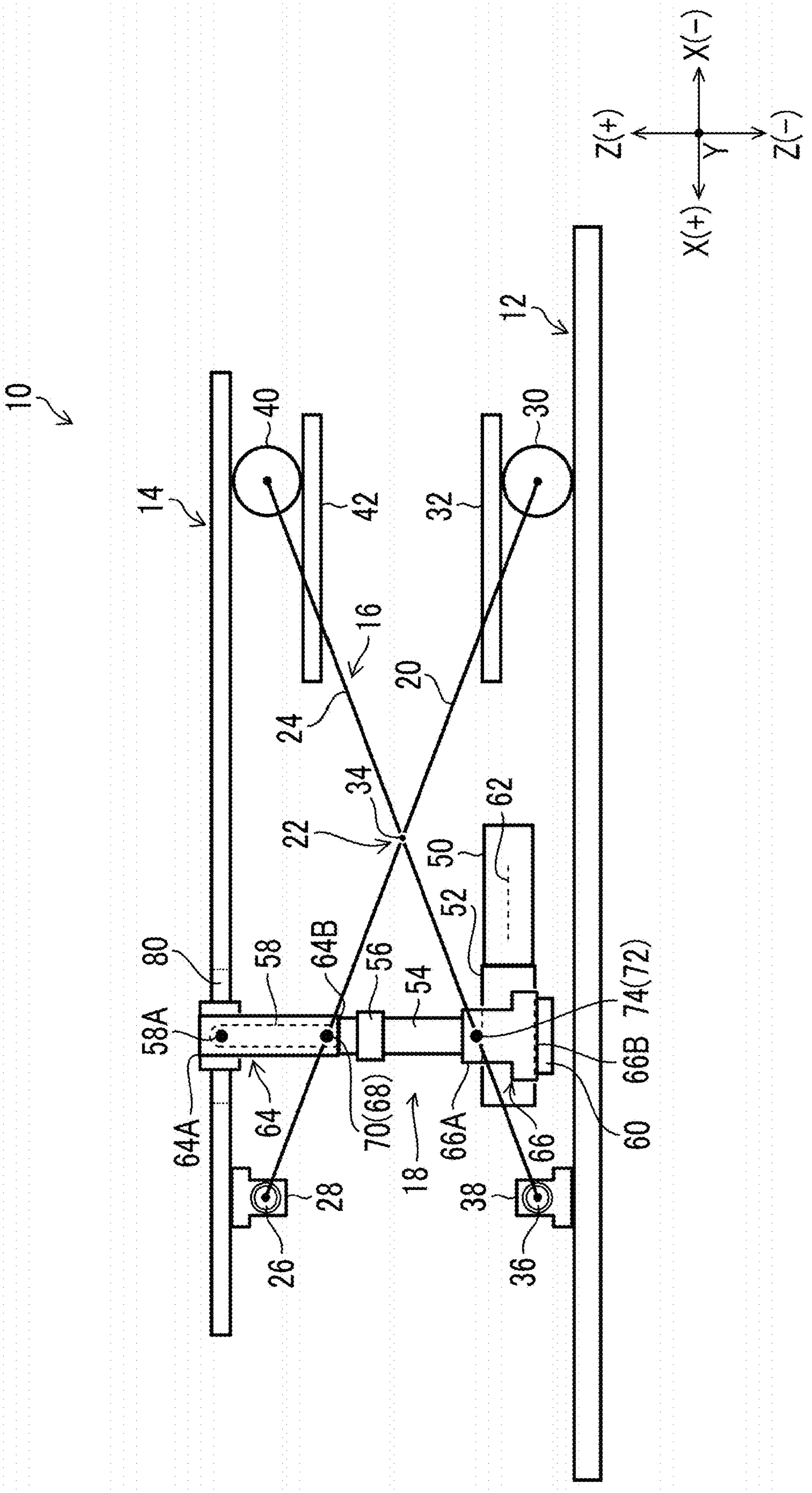
FIG. 6 is a schematic diagram showing a case in which the upper frame is located at the lowest height by the screw-type jack.

FIG. 5 is a schematic diagram of the bed apparatus 10 showing a state in which the upper frame 14 is located at the highest position by the driving force of the screw-type jack 18. FIG. 6 is a schematic diagram of the bed apparatus 10 showing a state in which the upper frame 14 is located at the lowest position by the driving force of the screw-type jack 18. The screw-type jack 18 is an example of an actuator according to the present invention.

As shown in FIGS. 5 and 6, the screw-type jack 18 includes a motor 50, a reducer 52, a cylinder 54, a nut 56, and a rod 58.

The motor 50 and the reducer 52 are mounted on a base 60 of the screw-type jack 18. The base 60 is a member that supports a lower end part of the screw-type jack 18. The cylinder 54 is connected to the reducer 52. The nut 56 is formed integrally with the cylinder 54. The rod 58 is inserted into the cylinder 54, and has a screw groove (not shown) formed on its outer circumferential surface to be screwed into a screw groove of the nut 56. The motor 50 is an example of a driving source according to the present invention, and the rod 58 is an example of a rod member according to the present invention.

The motor 50 is mounted on the base 60 such that a rotation axis 62 indicated by a dotted line in FIGS. 5 and 6 extends along the X axis. The reducer 52 converts rotation of the rotation axis 62 around the X axis into rotation around the Z axis, reduces a speed of the rotation, and transmits the speed-reduced rotation to the cylinder 54. In the present example, a reducer having a worm gear is illustrated as the reducer 52, but for example, a reducer having a bevel gear can also be used.

The cylinder 54 is connected to the reducer 52 such that a longitudinal axis (central axis) extends along the Z axis, and rotates around the Z axis due to the rotational force around the Z axis that is converted and reduced by the reducer 52. In a case in which the cylinder 54 rotates, the nut 56 provided on the same axis (Z axis) as the cylinder 54 rotates in the same direction around the Z axis.

In a case in which the cylinder 54 causes the nut 56 to rotate forward and backward around the Z axis, the rod 58 moves up and down (extends and retracts) along the Z axis due to a feeding action of the screw groove of the nut 56 and the screw groove of the rod 58. Since the rod 58 is connected to the first arm 20 via a jack arm 64 described below, the rod 58 moves up and down without rotating together with the nut 56.

With the screw-type jack 18 configured as described above, it is possible to move the upper frame 14 up and down by applying a certain thrust force in the up-down direction by the extension and retraction operation of the rod 58. Accordingly, the capacity (power) of the actuator can be reduced as compared with an actuator (for example, the actuator of JP2009-297145A) that raises and lowers the upper frame by applying a thrust force in a direction inclined with respect to the up-down direction.

In addition, the bed apparatus 10 according to the embodiment includes jack arms 64 and 66.

The jack arm 64 is a member that connects the rod 58 and the first arm 20 in the up-down direction (Z axis direction). The jack arm 66 is a member that connects the screw-type jack 18 (base 60) and the second arm 24 in the up-down direction (Z axis direction). The jack arm 64 is an example of a first connecting member according to the present invention, and the jack arm 66 is an example of a second connecting member according to the present invention.

The jack arm 64 is configured as a plate-shaped member having a longitudinal axis in the Z axis direction.

An upper end part 64A of the jack arm 64 is connected to an upper end part 58A of the rod 58. In addition, a lower end part 64B of the jack arm 64 is rotationally movably connected to an intermediate position 68 between the intersection part 22 (see FIG. 2) and the upper end part of the first arm 20 via a shaft 70 extending along the Y axis.

That is, the bed apparatus 10 according to the embodiment adopts, as a structure for transmitting the thrust force of the screw-type jack 18 to the upper frame 14, a structure in which the thrust force is transmitted from the upper end part 58A of the rod 58 via the jack arm 64 to the intermediate position 68 offset in the Z(−) direction (hereinafter, referred to as a "thrust force offset structure"). Here, a distance between a connecting point between the upper end part 64A of the jack arm 64 and the upper end part 58A of the rod 58 and a connecting point between the lower end part 64B of the jack arm 64 and the intermediate position 68 corresponds to a length of the offset.

The intermediate position 68 includes a range that is substantially recognized as the intermediate position. In addition, a position where the shaft 70 is provided is not limited to the intermediate position 68, and need only be a position between the intersection part 22 and the upper end part of the first arm 20. For example, the position may be a position shifted from the range that is substantially recognized as the intermediate position to the shaft 34 side or the shaft 26 side.

The jack arm 66 is configured as a plate-shaped member having a longitudinal axis in the Z axis direction.

A lower end part 66B of the jack arm 66 is connected to the base 60 that supports the lower end part of the screw-type jack 18. In addition, an upper end part 66A of the jack arm 66 is rotationally movably connected to an intermediate position 72 between the intersection part 22 (see FIG. 2) and the lower end part of the second arm 24 via a shaft 74 extending along the Y axis.

That is, the bed apparatus 10 according to the embodiment adopts a structure in which the screw-type jack 18 is suspended and supported from the intermediate position 72 of the second arm 24 via the jack arm 66, and the screw-type jack 18 is supported to be rotationally movable around the Y axis with the shaft 74 as the center (hereinafter, referred to as a "suspension rotational movement support structure").

As a result, the screw-type jack 18 can move up and down in conjunction with the raising and lowering operation of the pantograph arm 16 and can move in the X axis direction without changing its posture, that is, in a state in which the longitudinal axis of the rod 58 remains along the Z axis.

The intermediate position 72 includes a range that is substantially recognized as the intermediate position. In addition, a position where the shaft 74 is provided is not limited to the intermediate position 72, and need only be a position between the intersection part 22 and the lower end part of the second arm 24. For example, the position may be a position shifted from the range that is substantially recognized as the intermediate position to the shaft 34 side or the shaft 36 side.

Hereinafter, some comparative examples (Comparative Examples 1 and 2) will be compared with the embodiment. In describing the configuration of the bed apparatuses of Comparative Examples 1 and 2, illustrations thereof are omitted, but the same or similar members as those of the bed apparatus 10 according to the embodiment will be denoted by the same reference numerals.

Comparative Example 1

Comparative Example 1 is a bed apparatus in which the upper end part 58A of the rod 58 is connected to the upper frame 14, and the upper frame 14 is directly moved up and down by the extension and retraction operation of the rod 58.

Comparative Example 2

Comparative Example 2 is a bed apparatus in which the upper end part 58A of the rod 58 is connected to the intermediate position 68 of the first arm 20, and the pantograph arm 16 is raised and lowered by the extension and retraction operation of the rod 58, thereby indirectly moving the upper frame 14 up and down.

With respect to the bed apparatuses of Comparative Examples 1 and 2, the bed apparatus 10 according to the embodiment adopts the thrust force offset structure using the jack arm 64. As a result, the bed apparatus 10 according to the embodiment can move the upper frame 14 downward to a lower position by at least the offset length than in Comparative Example 1. In addition, since a stroke length of the rod 58 can be made longer by the offset length, the upper frame 14 can be moved downward to a lower position than in Comparative Example 2.

Therefore, with the bed apparatus 10 according to the embodiment, the configuration is adopted in which the jack arm 64 that connects the first arm 20 of the pantograph arm 16 and the rod 58 in the up-down direction is provided, and the upper end part 64A of the jack arm 64 is connected to the upper end part 58A of the rod 58 and the lower end part 64B of the jack arm 64 is rotationally movably connected to the position between the intersection part 22 and the upper end part of the first arm 20, so that it is possible to reduce (optimize) the capacity of the screw-type jack 18 while lowering the lowest height of the tabletop surface.

In addition, the bed apparatus 10 according to the embodiment adopts the suspension rotational movement support structure using the jack arm 66. As a result, it is possible to further move the upper frame 14 downward by a distance (gap) in the Z axis direction between the screw-type jack 18 (base 60) and the base 12 in FIG. 3. Therefore, it is possible to further lower the height of the lowest height of the tabletop surface.

In addition, as shown in FIG. 6, the upper frame 14 has an escape hole 80 (see FIG. 2) for allowing the upper end part 58A of the rod 58 to escape upward from the upper frame 14 in a case in which the upper frame 14 is moved downward.

By providing the escape hole 80 in the upper frame 14, a stroke length of the rod 58 can be made longer by a length of the rod 58 that protrudes from the upper frame 14 in the Z(+) direction. As a result, it is possible to further lower the lowest height of the tabletop surface.

It is preferable that a length of the rod 58 protruding from the escape hole 80 is set in accordance with a gap between the upper frame 14 and a tabletop (not shown) provided on an upper surface side of the upper frame 14.

Hereinafter, a modification example of the bed apparatus according to the embodiment of the present invention will be described.

Figure 7:
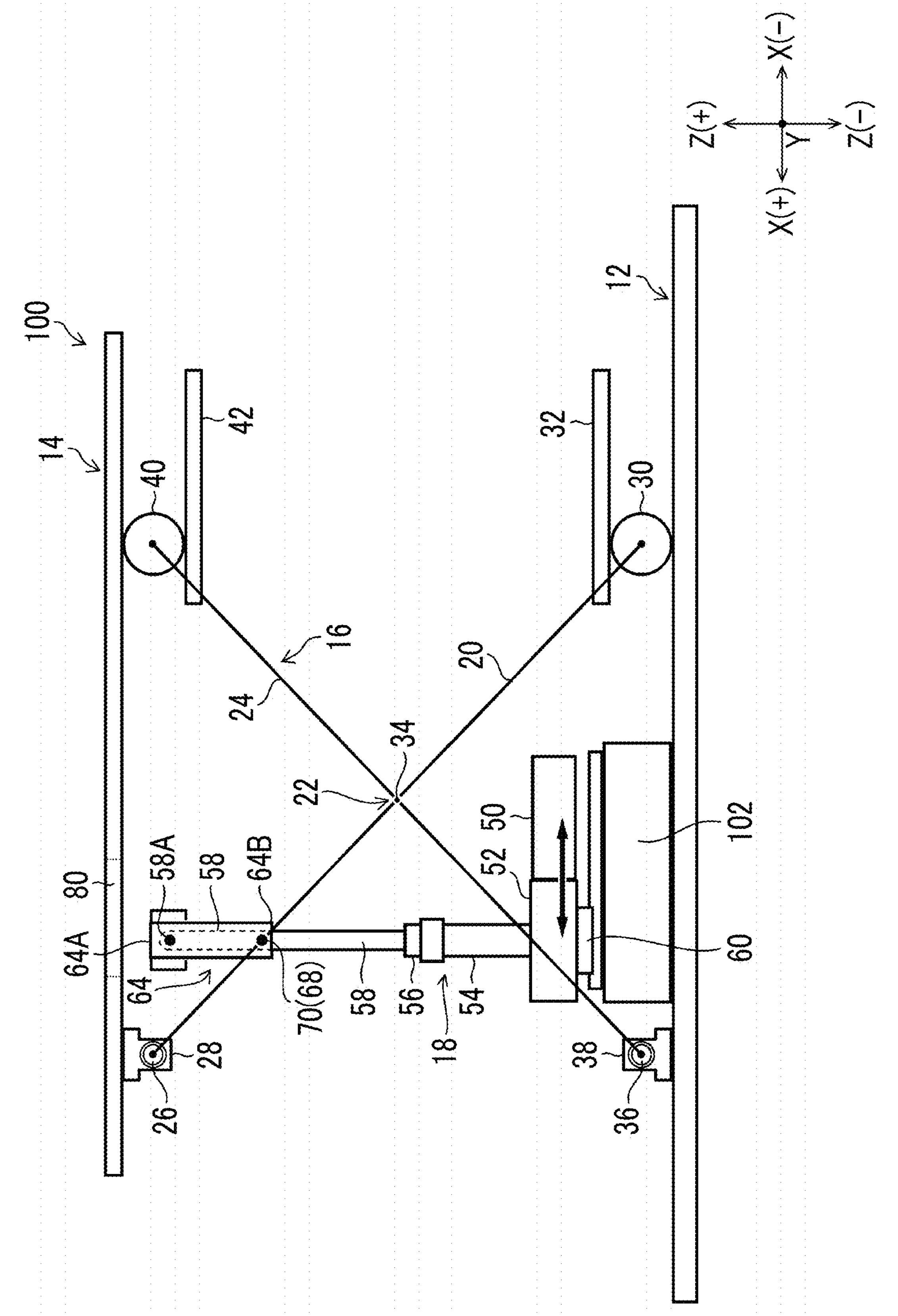
FIG. 7 is a schematic diagram of a bed apparatus according to a modification example.

FIG. 7 is a schematic diagram showing a modification example of the bed apparatus according to the embodiment of the present invention. A difference between the modification example shown in FIG. 7 and the embodiment shown in FIGS. 2 to 6 will be described.

First, the bed apparatus 10 according to the embodiment adopts the suspension rotational movement support structure using the jack arm 66. With respect to this, a bed apparatus 100 of the modification example shown in FIG. 7 adopts a structure in which the screw-type jack 18 (base 60) is mounted on a linear motion guide 102 and the screw-type jack 18 is provided to be slidably movable in the X axis (horizontal) direction by using the linear motion guide 102 (hereinafter, referred to as a "slide structure"). This point is the difference, and the other configurations are the same. The linear motion guide 102 is an example of a horizontal movement support portion according to the present invention.

The linear motion guide 102 is installed on the base 12. In addition, as the linear motion guide 102, a known linear motion guide that is a commercially available product can be applied.

With the bed apparatus 100 of FIG. 7, the screw-type jack 18 slidably moves in the X(+) direction and the X(−) direction in conjunction with the raising and lowering operation of the upper frame 14.

Even in a case in which the slide structure is adopted as in the bed apparatus 100 of FIG. 7, since the thrust force offset structure using the jack arm 64 is adopted, the capacity of the screw-type jack 18 can be reduced while lowering the lowest height of the tabletop surface as in the bed apparatus 10 according to the embodiment.

Although the bed apparatus according to the embodiment of the present invention has been described above, the present invention may be improved or modified in some ways without departing from the gist of the present invention.

EXPLANATION OF REFERENCES

10: bed apparatus
12: base
14: upper frame
16: pantograph arm
18: screw-type jack
20: first arm
22: intersection part
24: second arm
50: motor
58: rod
64: jack arm
66: jack arm
80: escape hole
100: bed apparatus
102: linear motion guide
150: MRI apparatus
200: medical diagnostic system

What is claimed is:

1. A bed apparatus comprising:
a base member;
an ascending and descending member;
an X-shaped pantograph arm including a first arm member and a second arm member that is connected to the first arm member at an intersection part so as to be rotationally movable with respect to the first arm member, the X-shaped pantograph arm connecting the ascending and descending member to the base member such that the ascending and descending member is able to ascend and descend in an up-down direction; and
an actuator that drives the pantograph arm,
wherein the actuator includes
a driving source,
a rod member that moves in the up-down direction by power of the driving source, and
a first connecting member that connects the rod member and the first arm member in the up-down direction,
wherein the first connected member has,
an upper end part connected to an upper end part of the rod member, and
a lower end part rotationally movably connected to a position between the intersection part and an upper end part of the first arm member.

2. The bed apparatus according to claim 1, further comprising:
a second connecting member that connects the actuator and the second arm member in the up-down direction and that has an upper end part rotationally movably connected to a position between the intersection part and a lower end part of the second arm member and a lower end part connected to a lower end part of the actuator.

3. The bed apparatus according to claim 1, further comprising:
a linear motion guide that supports the actuator to be movable in a horizontal direction.

4. The bed apparatus according to claim 1,
wherein the ascending and descending member has an escape hole for allowing the upper end part of the rod member to escape upward from the ascending and descending member in a case in which the ascending and descending member is moved downward.

5. A medical diagnostic system comprising:
the bed apparatus according to claim 1; and
a medical image capturing apparatus.

6. The medical diagnostic system according to claim 5,
wherein the ascending and descending member of the bed apparatus has an escape hole for allowing the upper end part of the rod member to escape upward from the ascending and descending member in a case in which the ascending and descending member is moved downward.

* * * * *